United States Patent [19]

Bray

[11] 4,220,452

[45] Sep. 2, 1980

[54] DETECTION OF GASES

[75] Inventor: Geddes A. Bray, Moston, Manchester, England

[73] Assignee: Mather & Platt Limited, Manchester, England

[21] Appl. No.: 6,718

[22] Filed: Jan. 26, 1979

[30] Foreign Application Priority Data

Feb. 7, 1978 [GB] United Kingdom ................ 4772/78

[51] Int. Cl.$^2$ ...................... G01N 31/12; G01N 33/22
[52] U.S. Cl. .............................. 23/232 R; 23/230 PC;
422/78; 422/94; 422/119
[58] Field of Search ........................ 23/230 PC, 232 R;
422/78, 94, 119; 73/23

[56] References Cited

U.S. PATENT DOCUMENTS

| 3,738,808 | 6/1973 | Cunningham et al. | 23/230 PC |
| 3,738,810 | 6/1973 | Clinton et al. | 23/230 PC |
| 4,033,897 | 7/1977 | Barnard, Jr. | 23/230 PC |

Primary Examiner—R. E. Serwin
Attorney, Agent, or Firm—Sughrue, Rothwell, Mion, Zinn and Macpeak

[57] ABSTRACT

A method of detecting the presence of a foreign gas in a gaseous medium of known combustion properties uses the fact that the percentage lower or upper explosive limits (LEL or UEL) of mixtures of any flammable gas in any other gas all have approximately the same varying relationship to the percentage LEL or UEL of the mixture as a whole when a known percentage of a reference gas of known combustion properties is added to the mixture. The method comprises the steps of mixing a sample of a possibly contaminated gaseous medium with known combustion properties in a fire-safe container (12), actuating ignition means (17) in an attempt to ignite the gaseous mixture in the container (12), and using detection means (18) to detect ignition or otherwise of the gaseous mixture to enable the presence of a foreign gas above a predetermined concentration in the gaseous medium to be detected. Apparatus for use in this method comprises in combination with the fire-safe container (12), means (15) for introducing the sample of possibly contaminated gas into the container, valve means for introducing a known quantity of the reference gas into the container, and ignition and detection means (17,18) to permit and monitor attempts at ignition of the sample.

22 Claims, 4 Drawing Figures

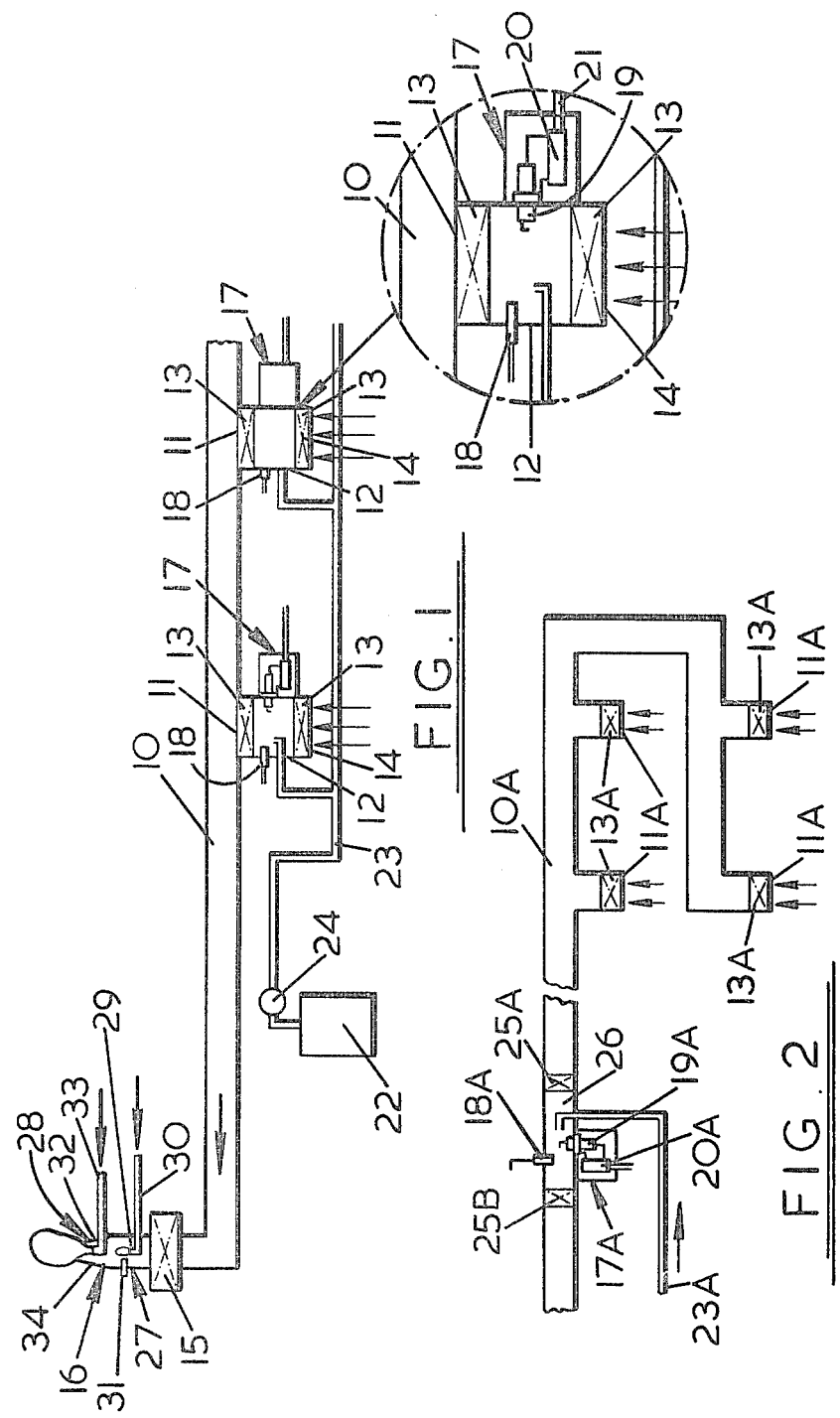

DETECTION OF GASES

The present invention relates to a method and apparatus for detecting the presence of gases or vapours in air or other gaseous media.

In industry as a whole, and particularly in the oil and chemical industries, the accidental release or leakage of flammable gases or vapours from process equipment is a serious fire and explosion hazard. Conventional methods of detecting such gases or vapours include a variety of chemical means, which have the disadvantage of being slow to operate and usually require visual observation. Other methods include the employment of solid state electrical devices, in which the surface state of a portion of the device changes its electrical resistance or di-electric strength when exposed to the appropriate gas, or the use of an electrically heated wire coil, usually made of platinum, which in the presence of a catalyst increases in temperature and hence in electrical response when the appropriate gas is burnt in the vicinity. In the latter method, an increase or decrease in the resistance of the coil may be detected to measure the appropriate gas concentration. However, these electrical methods are readily affected by extraneous substances which may poison the reactive material or catalyst and thereby ruin the detector.

The object of the present invention is to overcome the aforementioned disadvantages and provide an improved method of gas detection.

According to a first aspect of the present invention there is provided a method of detecting the presence of a foreign gas in a gaseous medium of known combustion properties, the method comprising the steps of mixing a sample of the possible contaminated gaseous medium with a known quantity of a reference gas of known combustion properties in a fire-safe container, and thereafter actuating ignition means in an attempt to ignite the gaseous mixture in the container, detection means being associated with the container whereby the ignition or otherwise of the gaseous mixture is monitored to enable the presence of a foreign gas above a predetermined concentration in the gaseous medium to be detected.

According to a second aspect of the present invention there is provided a gas detection arrangement for detecting the presence of a foreign gas in a gaseous medium of known combustion properties and comprising, in combination, a fire-safe container, means for introducing a sample of the possibly contaminated gaseous medium into the container, valve means for introducing a known quantity of a reference gas of known combustion properties into the container to mix with the gaseous medium therein, ignition means associated with the container to enable the resulting gaseous mixture within the container to be ignited if flammable, and detection means for monitoring the interior of the container to detect when ignition of said gaseous mixture takes place.

This method and apparatus are suitable not only for detecting the presence of flammable gas concentrations in air or other gaseous medium but also for detecting concentrations of dangerous non-flammable gas in air or other gaseous medium as before. Indeed, it will be appreciated that the present invention can be employed to detect the presence of any first gas in a second gas by using an appropriate reference gas where at least one of the components of the first, second, or reference gases are either flammable or supports combustion, the combustion properties of the reference gas and the second gas being known. Further, the invention is also suitable for detecting abnormal concentrations of a gas or gasses which may be normally present in the gaseous medium itself, for example an increased concentration of oxygen in air. However, for ease of description, the gas or vapour to be detected is referred to in the preceding paragraphs and hereinafter simply as the "foreign gas" and it is to be understood that this term includes within its scope pure gases, vapours, and gas or vapour mixtures, as well as increased concentrations of a gas or gases normally present in the gaseous medium itself. Similarly, the term "reference gas" is to be interpreted to include within its scopes pure gases, vapours, and gas and/or vapour mixtures.

A mixture of a relatively flammable gas with a non-flammable gas will explode or burn when ignited if the concentration of the flammable gas in the mixture lies between upper and lower limits which can be determined for the two gases. These limits are termed the upper an lower explosive limits UEL and LEL respectively, and are usually tabulated for any particular gas when mixed with air. It will be appreciated that below its LEL, the concentration of the gas is not sufficient to permit ignition whereas above the UEL there is not sufficient oxygen present in the air to permit ignition. However, in the ensuing description, the terms upper and lower explosive limits will be used in their general sense with reference to a mixture of any gas with another, oxygen being present as a constituent of either of the gases or the reference gas.

Examples of the present invention will now be described with reference to the accompanying drawings in which:

FIG. 1 is a diagram showing a first embodiment of a gas detection arrangement according to the present invention;

FIG. 2 is a diagram showing a second embodiment of gas detection arrangement;

Figure 3:
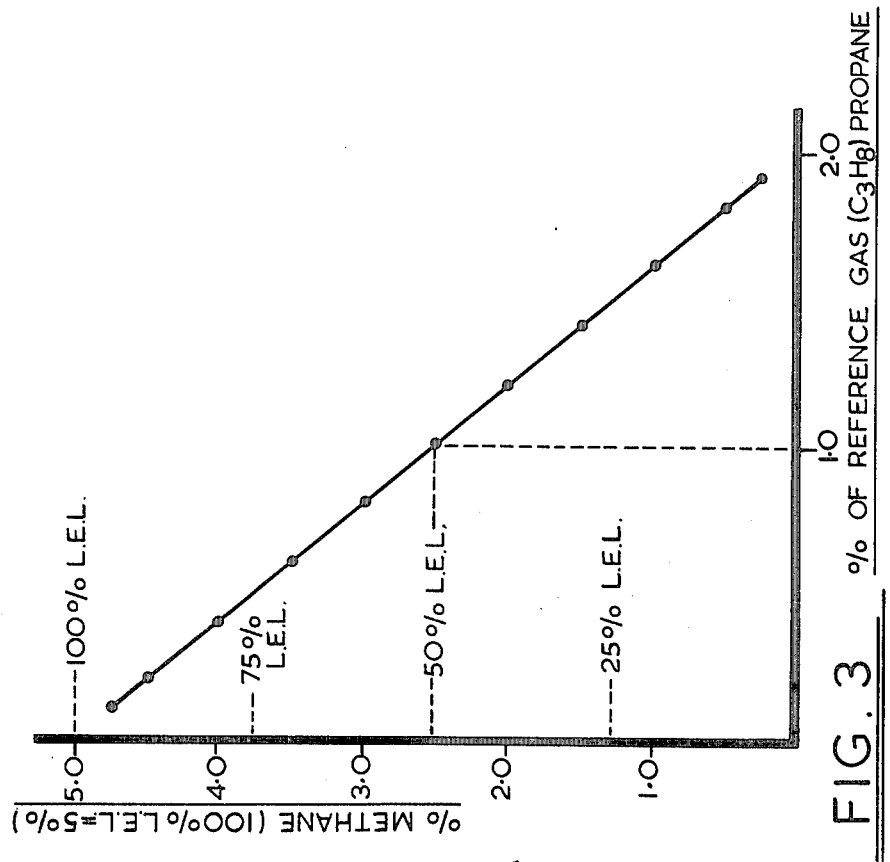
FIG. 3 is a graph showing, by way of example, the percentage concentration of propane as the reference gas required to detect varying concentrations of methane as the foreign gas in a gaseous medium.

As is stated above, a serious fire and explosion hazard arises from the leakage or accidental release of flammable gases from process equipment in industry. A gas detector operating according to the method of the present invention is particularly adapted to detect such flammable gases and is preferably linked to an alarm or warning system whereby a fire or explosion prevention procedure is initiated whenever the concentration of the flammable gas is found to be above a predetermined proportion less than but approaching the LEL of the gas or greater than but approaching the UEL of the gas.

As shown in FIG. 1, such a gas detection arrangement comprises a length of pipework 10 located in the area to be monitored. A single port or, as shown, a plurality of spaced ports 11 are arranged in the pipework 10 and to each of these ports 11 is connected a fire-safe container 12. Flame traps 13 are provided at the ports 11 to the pipework 10, which ports 11 form outlet ports from the containers 12 into the pipework 10, and at inlet ports 14 to the containers 12 from the atmosphere surrounding the pipework 10. The atmosphere to be tested around the pipework 10 is drawn therein by means of a fan 15 appropriately positioned in the pipework 10 downstream of the ports 11 as is described below. The rate of flow from the atmosphere surrounding the ports 14 into the containers 12 is adjustable to a constant level by valve or orifice means (not shown) or by suitable adjustment of the size of the flame traps 13. Thus, the inlet ports 14 form control orifices for determining entry of gas into the containers 12. Downstream of the fan 15 itself, the pipework 10 leads off into an exhaust system 16 which is also described below.

It will be appreciated that each of the containers 12 are non-flammable and fire sealed so that a flammable gas can be burnt therein without danger of ignition occurring either around the exterior of the pipework 10 or within it, gas having to pass through the flame traps 13 at the inlet and outlet ports 14 and 11 respectively of each container before reaching the interior of the pipe 10.

The flame traps 13 used can be of any known suitable type, for example each trap could comprise an air gap or gaps of a controlled depth and width across which gap flames are unable to pass. Alternatively, each container 12 could comprise a closed porous non-flammable fire-safe container so that the ports 11 and 14 are formed by respective end walls of the container. The principle of such a container is employed in the well known Davy lamp used down mines. In the present invention, however, the porous containers can be made of modern sintered materials.

Associated with each container 12 is an ignition means 17 such as can produce an electric spark and a detection device 18 such as a thermocouple, thermistor or pressure detector, which is preferably linked to a warning system as previously mentioned.

In the present example, the ignition means 17 comprises a sparking plug 19 which is connected to a suitable intermittent high voltage source, such as a coil 20 connected to an alternating current electricity supply of suitable frequency by electrical leads 21. A piezo-electric source could also be alternatively employed.

Each container 12 is also linked to a supply of a reference gas whereby a known quantity of this gas can be released into the container 12 at a predetermined rate via valve means (not shown). As shown in FIG. 1, this supply can take the form of a pressurised supply cylinder 22 connected via pipework 23 to each container 12 in turn. A stop valve 24 is also provided so that the supply of reference gas can be shut off. In modification a source of liquid vapour maintained at a controlled predetermined temperature could alternatively be used to provide the reference gas with the advantage that the vapour pressure of the reference gas is then always constant.

Where it is desired to detect the presence of a flammable gas, the reference gas will also be relatively flammable so that it is desirable to shield the pipework 23 carrying the reference gas from the supply cylinder 22 to each container 12 from the environment to be tested. One convenient way of doing this is to locate the latter pipework 23 within the main pipework 10 of the arrangement so that any leakage of the reference gas into the main pipework 10 will be removed safely by the fan 15.

In a second embodiment as shown in FIG. 2, the gas detection arrangement comprises a length of pipework 10A located in the area to be monitored and provided with a plurality of spaced ports 11A each of which is formed by a control orifice and is covered by a flame trap 13A. Hence, the interior of the pipework 10A is separated from the surrounding atmosphere only by means of the flame traps 13A, which may be of any known suitable type as mentioned above in the first embodiment of FIG. 1.

Downstream of all the ports 11A in the pipework 10A, there is preferably located a flame trap 25A and downstream of this trap 25A is located, spaced therefrom, a second flame trap 25B whereby a fire-safe chamber or container 26 is defined within the pipework 10A itself. In a similar fashion to each of the containers 12 described above with reference to FIG. 1, this container 25 is provided with an ignition means 17A, comprising a sparking plug 19A and coil 20A and a detection device 18A. Additionally, a supply of reference gas is linked to the container 26 via pipework 23A and valve means (not shown) as in the FIG. 1 embodiment.

In order that the atmosphere surrounding the pipework 10A can be drawn therein and into the container 26, a fan (not shown) is positioned in the pipework 10A downstream of the container 26. An exhaust system (not shown) for the pipework 10A as is described below is also provided downstream of the container 26.

In use, both the FIG. 1 and FIG. 2 embodiments of the detection arrangement operate in a similar fashion. The atmosphere surrounding the pipework 10, 10A is drawn continuously therein by means of the fan and enters the fire-safe containers 12 or the container 26.

To detect the presence of a foreign gas as its concentration approaches its LEL, this atmospheric gas will comprise the known gaseous medium of predetermined combustion properties and may also comprise a proportion of the foreign flammable gas. A known quantity of the reference gas lower than its LEL in the gaseous medium is either continuously or periodically released into the sample of gas in each container 12 or 26 so that these gases mix, the particular quantity of reference gas having been predetermined according to the pressure within containers 12 or 26. Periodically or at predetermined times thereafter an electric spark is produced by activating the ignition means 17, 17A and if ignition occurs the thermal detection device 18, 18A will register a signal and thereby trigger the associated warning system.

It will be appreciated that the arrangement of FIG. 1 can be used in two different ways. Firstly, with a plurality of containers 12, each container 12 can be located in a region which it is desired to monitor continuously so that each container 12 is used simultaneously with the others. Alternatively, however, the controls for the ignition and detection means 17 and 18 of each container 12 could be operated selectively so that spot check can be made on the particular region covered by the container as desired. Cyclic operation is also possible so that each region covered by a container can be checked in turn periodically.

The arrangement of FIG. 2 has only one detection container 26 associated with a plurality of inlet ports 13A. Hence, in this embodiment the foreign gas content of the gaseous medium surrounding the pipework 10A is averaged over each of the regions in which each of the ports 13A are located. The detection container 26 in this embodiment may be located outside the regions to be monitored.

To ensure reliability and accuracy of detection, the reference gas must be selected and quantised according to the particular foreign gas or range of foreign gases which are to be detected for any given gaseous medium. It will be realised that the present invention can be used for simple alarm purposes, in which it is only desired to know whether the foreign gas is present in concentrations approaching a dangerous level, but it can also be used for determining the concentration of the foreign gas with some accuracy. In, the latter case the LEL of the foreign gas in the gaseous medium must be known so that the percentage LEL of the foreign gas in the sample can be determined by release of an appropriate quantity of reference gas at each test. Butane and particularly propane are two reference gases which can be used to detect flammable gases using the aforedescribed arrangements and it can be seen that these gases can also be used as reference gases when it is desired also to detect their presence as foreign gases.

FIG. 3 is a graph illustrating the use of propane as a reference gas when it is desired to detect methane as the foreign gas in air. In air, methane has an LEL of 5% concentration. Hence, if it is desired to detect the presence of methane at a concentration of say at least 2.5%, then it can be seen that the minimum concentration of propane required within the container to cause ignition is approximately 1.0%. Thus, by controlling the quantity of propane released into the container so that a desired concentration is obtained and attempting ignition for a range of methane gas concentrations, the approximate concentration of methane can be determined. The purpose of many installations, however, will be to give a warning when the concentration of a flammable foreign gas in air exceeds a predetermined level so that the same quantity of reference gas can be released for each attempt at ignition. The percentage LEL of the flammable foreign gas or mixture of flammable gases in air will have approximately the same relationship to the percentage of reference gas as does methane to the propane reference gas as shown in FIG. 3.

Once ignition occurs in any fire-safe container 12 or 26, burning will continue therein until checked as long as flammable gas is present. The burnt gaseous products are drawn into the pipework 10, 10A by the fan to be safely disposed of by the exhaust system.

For ignition to occur in the fire-safe containers 12 or 26, sufficient oxygen must be present therein. Such oxygen may form or be a constituent or the gaseous medium or the foreign gas. However, if the gaseous medium is air or other gas containing oxygen then the release of the sudden large quantity of foreign gas may swamp a particular fire-safe container 12 or 26, so that when ignition is attempted therein, insufficient oxygen is present to initiate burning, i.e. the concentration of the foreign gas within the container is above the UEL. Hence, until this quantity of foreign gas becomes sufficiently diffused around the particular container 12 or inlet ports 13A in question, no warning will be given although clearly there is a significant fire and/or explosion risk. There are two ways of overcoming this problem so that a rapid warning can be given of the presence of large quantities of foreign gas in the area being monitored.

The first solution to the problem is to add oxygen to the gaseous mixture in the fire-safe container 12 or 26 before ignition is attempted. This can be conveniently done by adding oxygen as the reference gas. However, the use of oxygen in this manner can itself produce a fire and explosion hazard. The second and more preferable solution involves the use of a back-up detection system which is conveniently associated with the exhaust system as will now be described.

The gaseous mixture to be disposed of may comprise any of the following mixtures:
  (i) the gaseous medium mixed with reference gas, no foreign gas being present so that no combustion has taken place; or
  (ii) the burnt products of the gaseous medium, foreign gas and reference gas; or
  (iii) a large quantity of foreign gas mixed with reference gas and a little of the gaseous medium.

These gaseous mixtures may be safely disposed off at a location remote from the area being monitored either by being diluted or by being burnt off.

Reffering to FIG. 1, the exhaust system 16 is located downstream of the fan 15 and comprises a back-up detection system 27 for burning a reference flame within the main pipework 10 and means 28 for burning off the exhaust gases to be disposed of from the containers 12.

The back-up detection system 27 comprises an independent gas burner 29 which is located immediately downstream of the fan 15 and fuelled by an independent gas supply via a pipe 30. The particular gas used for the burner 29 is dependent on the exhaust gases which are expected to be present within the pipework 10 as fluctuations in the constituents and concentrations of these exhaust gases will affect the physical characteristics of the reference flame. For example, the temperature, intensity, colour or size of the reference flame may vary accordingly to the surrounding gaseous atmosphere. These changes can be detected by means of an appropriate detector 31 mounted within the pipework 10 adjacent the burner 29 and linked to the warning system associated with the detection devices 18. Hence, it is possible to confirm the results of the controlled ignition of the gases carried out within the containers 12 or otherwise. In particular, should the containers 12 be swamped by a large quanity of foreign gas, for example oxygen and, therefore, not indicate the presence of same, the reference flame will be affected so that the warning system will be triggered by the signal from the detector 31. Indeed, in some instances the reference flame itself may be extinguished to trigger the warning system. Where this is likely to happen, the burner 29 can be associated with means (not shown) for the automatic re-lighting of same such as a sparking device.

The means 28 for burning off the exhaust gases comprises a second larger burner 32 which is also supplied with gas from an independent source via a pipe 33. The burner 32 is located at an end of the pipework 10 formed into a jet 34 at a location where it is safe to burn off gases in the atmosphere, and the exhaust gases in the pipework 10 are entrained in the flame of the burner 32. It will be appreciated that unless a high quantity of flammable gas is present in the exhaust gases it is necessary to supply the extra flammable gas to the burner 32 to cause the gases to be burnt. This is particularly important where flammable foreign gas is present in the exhaust gas which was not burnt in the containers 12. The flame produced at the burner 32 can also be provided with monitoring means and also relighting facilities.

Figure 4:
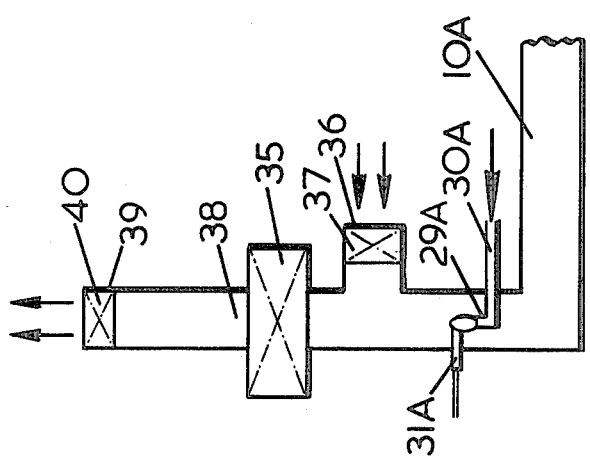
FIG. 4 is a diagram showing an exhaust system forming a part of a gas detection arrangement according to the present invention.

FIG. 4 shows an alternative exhaust system such as could be used and as now will be described in association with the embodiment of invention described above with reference to FIG. 2. In this system the back-up detection system is located in the pipework 10A upstream of the fan 35 for drawing gas therethrough. As in the previous embodiment, the back-up system comprises a burner 29A supplied with gas from an independent source via a pipe 30A. A detector 31A is associated with the burner 29A and the arrangement operates in an identical fashion to that already described.

Downstream of the back-up detection system is an inlet port 36 in the pipework 10A, which port 36 is covered by a flame trap 37. The port 36 is located upstream of the fan 35 and is open to a source of non-contaminated air or other non-toxic or non-inflammable gas which is drawn into the pipework 10A to mix with the exhaust gases in a chamber 38 formed downstream of the fan 35 by the pipework 10A. In this way the exhaust gases can be diluted sufficiently for the resulting mixture or gases to be safely discharged into the atmosphere at an appropriate location. This discharge is accomplished at an end 39 of the pipework 10A, which end 39 may form a chimney and is covered by a further flame trap 40.

In both embodiments of exhaust system as described above the fan 15 and 35 can be replaced by a positive displacement pump so that the effect of gas pressure differences in the atmosphere around the pipework 10, 10A, such as could be caused by wind or other weather affects, is reduced.

A further modification could also be made to the exhaust system as described with reference to FIG. 1, in which a heat sensor or other suitable detector is associated with the flame caused by the exhaust gases being burnt off and linked to the warning system. This arrangement could be used in association with the back-up detection system or as an alternative to it.

In all the embodiments of exhaust system described above the further gases used may be town or natural gas which is comparatively cheap and plentiful and which does not need to be added to the exhaust gases in the same predetermined and quantised fashion as the reference gas.

Further checks and monitoring systems may also be included in the detection arrangements described above. For example, the ignition system can be electrically monitored and the warning system can be periodically checked by either automatically or manually increasing the reference gas flow rate to the fire-safe container to a level above the LEL of the reference gas in the gaseous medium so that the warning system will be triggered. The alarm so raised can be suppressed for test purposes. Similarly, the reference gas pressure can be monitored which will give an indication of leaks or pressure reduction from any other course, such as damage to pipelines. This is particularly important when the reference gas itself is comparatively flammable with regard to fire hazards which may be in the vicinity. Further the fan drawing the gaseous medium and foreign gas into the fire-safe containers can be supervised by reference to its suction pressure.

All of the aforementioned monitoring devices, together with the detectors of the detection system itself can be linked to a main control panel where the whole installation can be constantly supervised for correct operation. Arrangements may be made to shut down operation of the installation after a warning has been given or after a number of cycles producing warnings have occurred.

As previously stated, the present invention is not limited to the detection of the presence of a flammable gas in the comparatively non-flammable gas but can be used for detecting the presence of any gas in any other where the flammable properties of the gases differ. If it is desired to detect dangerous concentrations of non-flammable gases, for example halons, in a gaseous medium the arrangements described above can be easily modified to do this. It will be appreciated that in this case it is convenient to test for oxygen deficiency in the fire-safe containers. Hence, the supply of reference gas to the containers is fixed so that under normal conditions, when no foreign gas is present, the concentration of reference gas in the gaseous medium is above the LEL so that ignition always takes place. When a predetermined concentration of foreign gas is present, however, the quantity of oxygen in the fire-safe container is so reduced that no ignition takes place and a warning can be given. It can be seen that in this case, the gaseous medium or the reference gas must contain oxygen and that the thermal detection system must trigger the warning system when no ignition takes place. In this case it is also possible to use the back-up detection system coupled to the exhaust system as the presence of a non-flammable gas will affect the reference flame.

In this latter application, it is possible to use a variation of the back-up detection system without reference to the main detection system. For example, a portable fire-safe container could be used in which a gas-fuelled flame is kept constantly burning monitored by a thermocouple with a meter readout could be used to indicate changes in flame temperature caused by the presence of non-flammable gases. A similar portable device could also be used for detecting the presence of flammable gases with suitable alteration.

It is also possible to check whether some gaseous mixtures contain a foreign gas above the UEL by carrying out tests to ensure there is no ignition when no reference gas is added to the gaseous mixture and that ignition takes place when an oxidising reference gas is added to the gaseous mixture. In these cases it is convenient to use air or oxygen as the reference gas and it can be seen that, in practice, the concentration of the foreign gas can be monitored so that a warning is given as the concentration falls below a predetermined level approaching the UEL.

It will be appreciated, therefore, in view of the foregoing description that the method of gas detection according to the present invention provides a rapid response with no possibility of poisoning or wide variation in sensitivity. Further, the method can be used to detect many different gases, the apparatus used being appropriately calibrated and adjusted according to the type of gas to be detected. The method is also suitable for use both exterior to and within the interior of tanks, vats and the like in use in industry which have a gaseous atmosphere which it is desirable to monitor.

What is claimed is:

1. A method of detecting the presence of a foreign gas in a gaseous medium of known combustion properties, comprising the steps of:
    (a) providing a pipework arrangement defining a plurality of inlet ports;
    (b) continuously drawing into the pipework arrangement via the inlet ports a possibly contaminated gaseous medium at a known rate;
    (c) providing a fire safe container which forms a port of the pipework arrangement and which defines an inlet and an outlet;

(d) providing flame traps associated with the inlet and outlet of the fire safe container;

(e) passing samples of the possibly contaminated medium through the fire safe container via the inlet and outlet through the flame traps;

(f) supplying a reference gas of known combustion properties to the fire safe container at a known rate;

(g) continuously mixing the sample in the fire safe container with the reference gas;

(h) providing ignition means within the fire safe container;

(i) actuating the ignition means to attempt to ignite the gaseous mixture in the fire safe container;

(j) providing an exhaust system for the pipework arrangement;

(k) ducting the gaseous mixture drawn from the fire safe container to the exhaust system for safe disposal;

(l) providing detection means associated with the fire safe container whereby ignition of the gaseous mixture within the fire safe container can be checked; and (m) monitoring the detection means whereby the presence of a foreign gas above a predetermined concentration in the gaseous medium can be detected.

2. A method as claimed in claim 1, comprising the additional step of, within the exhaust system, mixing the aforesaid gaseous mixture with a flammable gas and burning the resulting gaseous mixture.

3. A method as claimed in claim 1, comprising the additional step of, within the exhaust system, mixing the aforesaid gaseous mixture with another gas to dilute the former and thereafter releasing the resulting gaseous mixture into the atmosphere.

4. A method as claimed in claim 1, comprising the additional step of providing a back-up detection system and, after ignition has been attempted, ducting the gaseous mixture within the container to the back-up detection system.

5. A method as claimed in claim 4, in which the back-up detection system comprises the burning of a reference flame of a second flammable reference gas in an atmosphere comprising the exhausted gaseous mixture, providing second detection means associated with the back-up detection system, and monitoring the reference flame by the second detection means whereby any variation of the reference flame caused by changes in the exhausted gaseous medium can be monitored.

6. A method as claimed in claim 3, comprising the additional step of providing a back-up detection system and, after ignition has been attempted, of ducting the gaseous mixture within the container to the back-up detection system, the back-up detection system comprising a second detection means whereby the flame created by the burning of said resulting gaseous mixture and any variation of the flame caused by changes in the exhausted gaseous medium can be monitored.

7. A method as claimed in claim 1, in which a plurality of samples of possibly contaminated gaseous media are taken from a variety of locations within a region which it is desired to monitor and are mixed together to provide a single sample for testing whereby the possible foreign gas contents of the gaseous medium is averaged over said region.

8. A gas detection arrangement for detecting the presence of a foreign gas in a gaseous medium of known combustion properties and comprising, in combination:

(a) a pipework arrangement defining a plurality of inlet ports;

(b) a fire safe container which forms a part of the pipework arrangement and which defines an inlet and an outlet;

(c) flame traps associated with the inlet and outlet of the fire safe container;

(d) means for continuously drawing a possibly contaminated gaseous medium into the pipework arrangement via the inlet ports and thereby introducing a sample of the possibly contaminated gaseous medium into the fire safe container via the flame trap associated with the inlet of the container;

(e) flow regulation means for introducing a reference gas of know combustion properties into the fire safe container at a known rate to mix with the sample of the gaseous medium therein;

(f) ignition means associated with the fire safe container to enable the resulting gaseous mixture within the fire safe container to be ignited if flammable;

(g) detection means for monitoring the interior of the fire safe container to detect if and when ignition of the gaseous mixture takes place; and (h) an exhaust system associated with the pipework arrangement to which the gaseous mixture drawn from the fire safe container can be ducted for safe disposal.

9. An arrangement as claimed in claim 8, in which the fire safe container comprises a closed non-flammable container, the walls of which container define porous inlet and outlet areas through which the gaseous medium must pass to enter and to leave same.

10. An arrangement as claimed in claim 8, in which the fire safe container comprises a non-flammable container with an inlet port and an outlet port each covered by a flame trap.

11. An arrangement as claimed in claim 8, in which the ignition means comprises a sparking plug connected to an electricity supply.

12. An arrangement as claimed in claim 8, in which the means for drawing the sample into the fire safe container comprises a fan.

13. An arrangement as claimed in claim 8, in which the means for drawing the sample into the fire safe container comprises a positive displacement pump.

14. An arrangement as claimed in claim 8, in which the means for drawing the sample into the fire safe container is located in said pipework arrangement downstream of the fire safe container but upstream of the exhaust system.

15. An arrangement as claimed in claim 14, in which the exhaust system comprises a first burner located at one end of the pipework and fuelled by a flammable gas, the end of said pipework defining a jet whereby the gaseous mixture can be burnt off by the burner.

16. An arrangement as claimed in claim 14, in which the exhaust system defines a chamber downstream of said means for drawing the sample into the fire safe container wherein the gaseous mixture can be diluted by another gas drawn into the chamber via a port defined by the pipework upstream of said means, the diluted gaseous mixture being dischargeable to the atmosphere from an end of the pipework covered by a flame trap.

17. An arrangement as claimed in claim 8, which additionally comprises a back-up detection system wherein a reference flame is burnt in an atmosphere formed by the gaseous mixture exhausted from the container after ignition has been attempted.

18. An arrangement as claimed in claim 17, in which the back-up detection system comprises a reference burner for the reference flame fuelled by a second reference gas and located in the pipework downstream of the container, a detector being located in proximity to the burner whereby any variation of the flame caused by changes in the exhausted gaseous mixture can be monitored.

19. An arrangement as claimed in claim 18, in which the exhaust system comprises a first burner located at one end of the pipework and fuelled by a flammable gas, the end of said pipework defining a jet whereby the gaseous mixture can be burnt off by the burner, the reference burner being located in the pipework downstream of said drawing means but upstream of the jet.

20. An arrangement as claimed in claim 18, in which the back-up detection system comprises a reference burner for the reference flame fuelled by a second reference gas and located in the pipework downstream of the container, but upstream of the drawing means, a detector being located in proximity to the burner whereby any variation of the flame caused by changes in the exhausted gaseous mixture can be monitored.

21. An arrangement as claimed in claim 17, in which the back-up detection system comprises a detector located in proximity to the first burner whereby any variation of the flame caused by changes in the exhausted gaseous medium can be monitored.

22. An arrangement as claimed in claim 8, in which the fire safe container is associated with a plurality of inlet ports in the pipework whereby the sample of possibly contaminated gaseous medium is taken from a variety of locations within a region covered by the pipework via the inlet ports to average the possible foreign gas contents of the gaseous medium over said region.

* * * * *